United States Patent
O'Donnell

(10) Patent No.: US 6,808,486 B1
(45) Date of Patent: Oct. 26, 2004

(54) SURGICAL INSTRUMENT FOR TREATING FEMALE URINARY STRESS INCONTINENCE

(75) Inventor: Pat D. O'Donnell, Tulsa, OK (US)

(73) Assignee: Pat O'Donnell, Springfield, IL (US)

( * ) Notice: Subject to any disclaimer, the term of this patent is extended or adjusted under 35 U.S.C. 154(b) by 45 days.

(21) Appl. No.: 10/308,735

(22) Filed: Dec. 3, 2002

(51) Int. Cl.⁷ ................................................. A61F 2/02
(52) U.S. Cl. ....................................................... 600/30
(58) Field of Search ........................ 600/38–41, 29–31; 128/897, 898; 606/151

(56) References Cited

U.S. PATENT DOCUMENTS

| | | | |
|---|---|---|---|
| 4,052,988 A | 10/1977 | Doddi et al. | |
| 4,441,496 A | 4/1984 | Shalaby et al. | |
| 4,452,245 A | * 6/1984 | Usher | 606/151 |
| 4,564,013 A | 1/1986 | Lilenfeld et al. | |
| 5,112,344 A | 5/1992 | Petros | |
| 5,578,046 A | 11/1996 | Liu et al. | |
| 5,626,611 A | 5/1997 | Liu et al. | |
| 5,686,090 A | 11/1997 | Schilder et al. | |
| 5,899,909 A | 5/1999 | Claren et al. | |
| 6,031,148 A | 2/2000 | Hayes et al. | |
| 6,042,534 A | 3/2000 | Gellman et al. | |
| 6,093,200 A | 7/2000 | Liu et al. | |
| 6,273,852 B1 | 8/2001 | Lehe et al. | |
| 6,315,788 B1 | 11/2001 | Roby | |
| 6,406,423 B1 | * 6/2002 | Scetbon | 600/30 |
| 6,423,080 B1 | * 7/2002 | Gellman et al. | 606/148 |
| 6,638,210 B2 | * 10/2003 | Berger | 600/30 |
| 6,638,211 B2 | * 10/2003 | Suslian et al. | 600/30 |
| 6,652,450 B2 | * 11/2003 | Neisz et al. | 600/30 |
| 6,702,827 B1 | * 3/2004 | Lund et al. | 606/151 |
| 2002/0107430 A1 | 8/2002 | Neisz et al. | |
| 2002/0128670 A1 | * 9/2002 | Ulmsten et al. | 606/151 |
| 2002/0156489 A1 | * 10/2002 | Gellman et al. | 606/139 |

* cited by examiner

Primary Examiner—Samuel G. Gilbert
(74) Attorney, Agent, or Firm—Ray Norton

(57) ABSTRACT

A surgical instrument for treating female urinary stress incontinence comprising a tubular mesh sling for implanting into the lower abdomen of a female which provides support to mid-urethral and bladder neck sphincteric continence sites with the sling defining in part, plastic sheath portions fixedly attached to opposite ends of a tubular mesh section. The tubular mesh sling is deployed via a sling transfer instrument having distal and proximal ends with the instrument comprising in part a progressively curved shaft portion positioned between the distal and proximal ends. A handle is located on the instrument's proximal end and a tip portion on the instrument's distal end. Both a transvaginal instrument and a suprapubic instrument for sling transfer is disclosed as is a spacing device used to position the sling without tension.

29 Claims, 17 Drawing Sheets

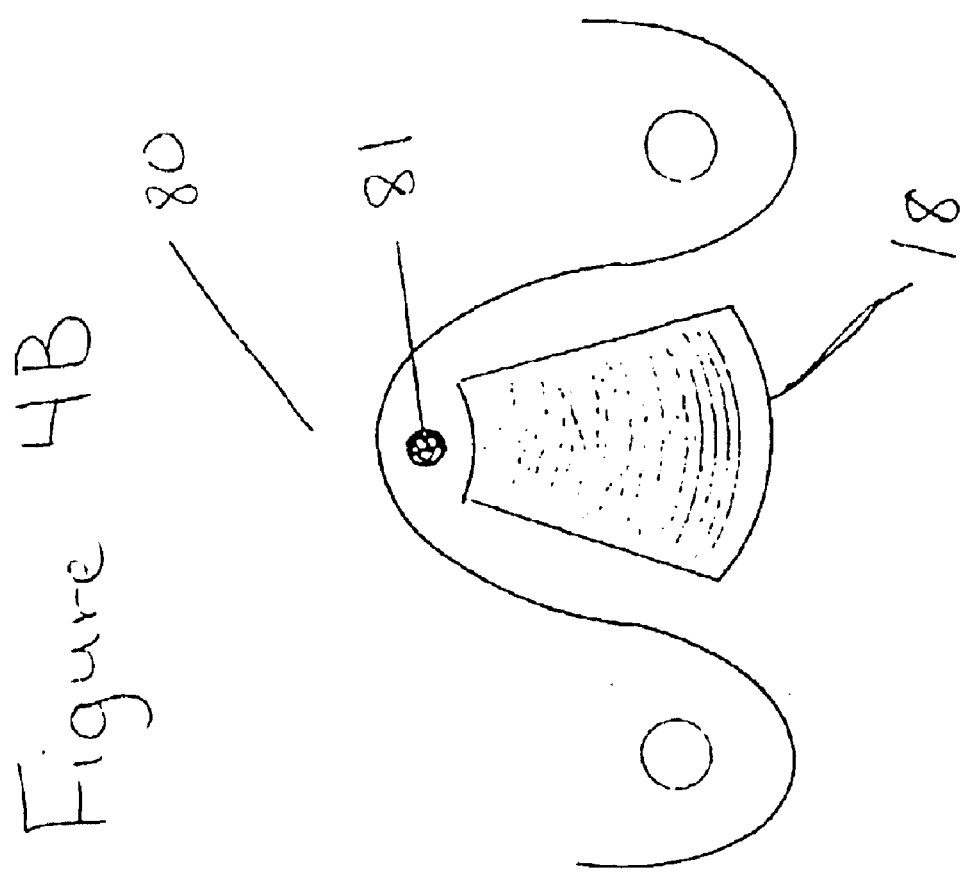

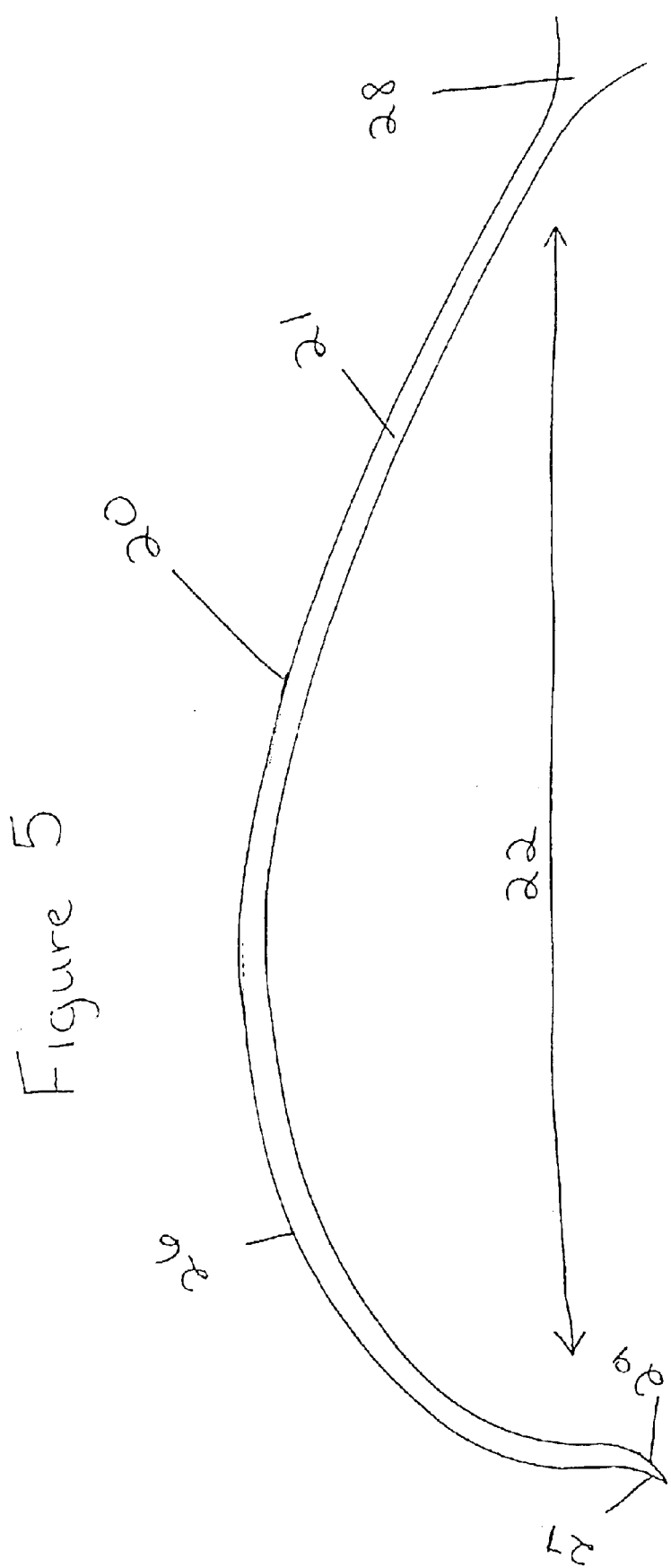

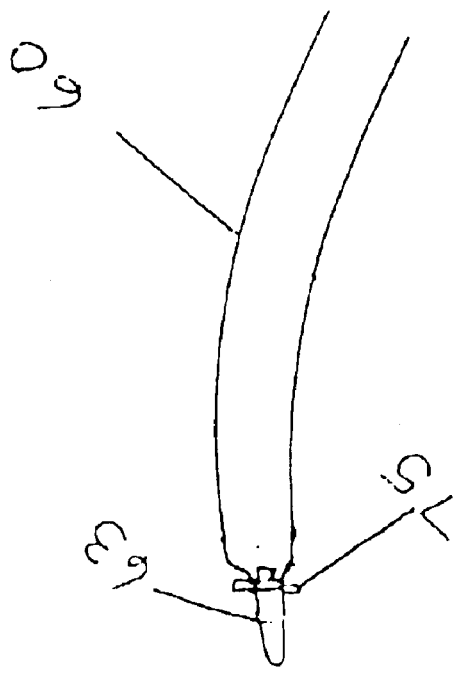
Figure 11
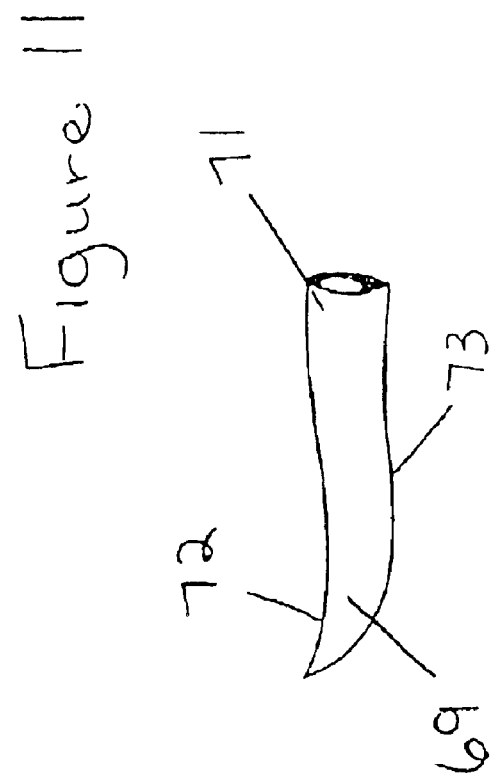
Figure 11B
Figure 11A
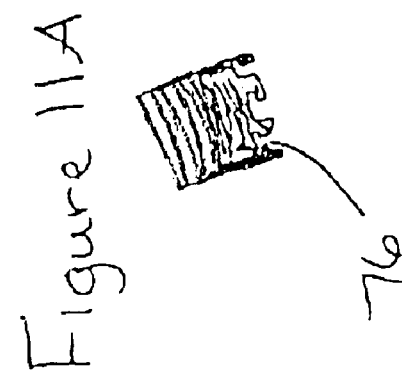

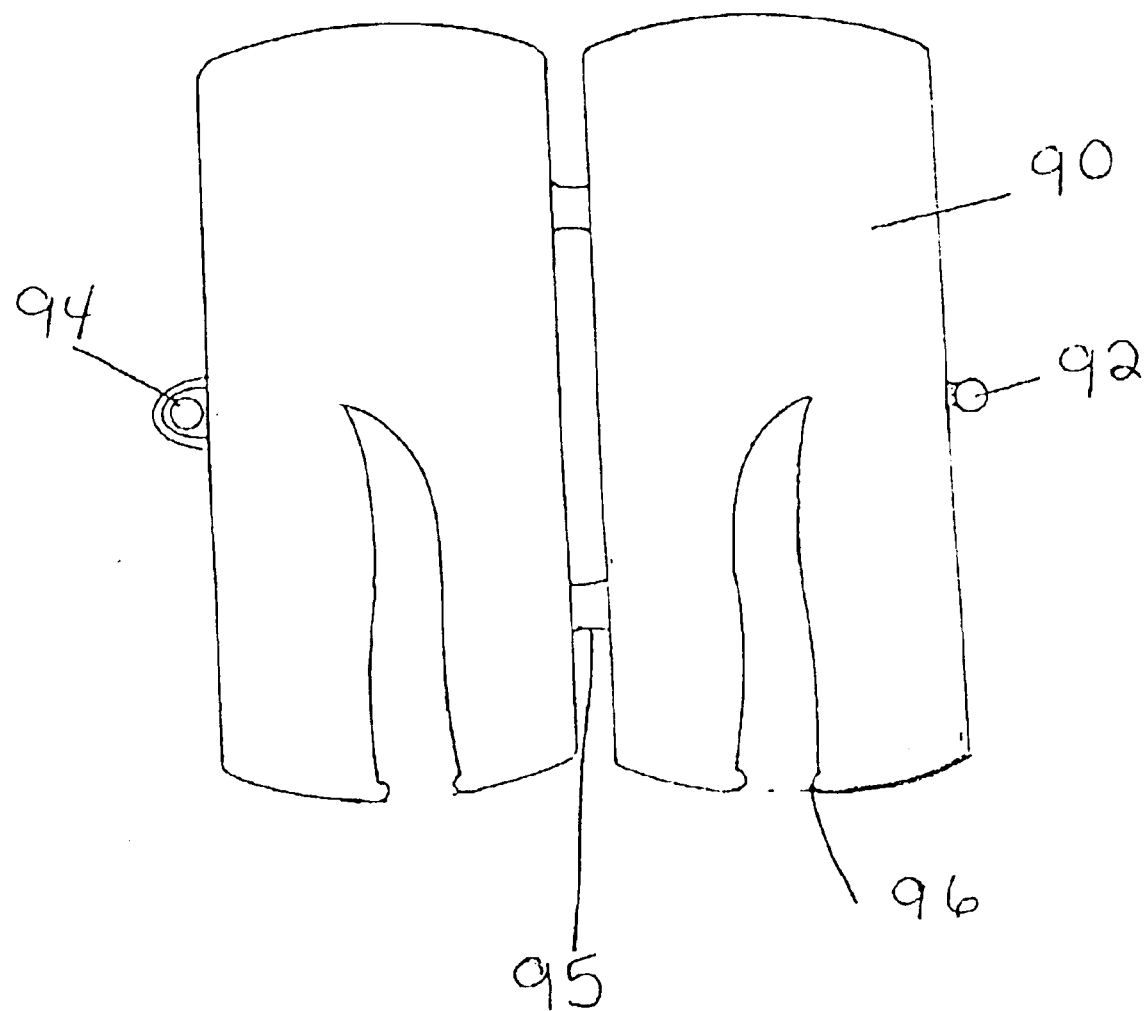

SURGICAL INSTRUMENT FOR TREATING FEMALE URINARY STRESS INCONTINENCE

TECHNICAL FIELD OF THE INVENTION

The present invention relates to surgical instruments for treating female urinary stress incontinence problems generally and in particular, a tubular mesh sling for implanting into the lower abdomen of a female which provides support to mid-urethral and bladder neck sphincteric continence sites.

BACKGROUND OF THE INVENTION

Pubovaginal sling surgical procedures for treatment of stress urinary incontinence in women are based historically on many clinical studies that show excellent results utilizing autologous rectus fascia. In the classic pubovaginal sling procedure, a strip of rectus fascia is removed from the anterior abdominal wall of the patient and the tissue is transplanted to the anterior vaginal wall to provide anatomical support to the bladder neck continence site. The long term continence results from this operative technique have been superior to other surgical procedures, especially in women who have very poor function of the urethra.

Women who have a rectus fascia pubovaginal sling procedure experience significant postoperative discomfort that results from harvesting the fascia from the anterior abdominal wall. Although rectus fascia has excellent tensile strength and superb long term durability, it has very little elasticity. Consequently, postoperative urinary retention is a problem if the sling is placed with tension around the urethra. Urethral obstruction and difficulty voiding are common postoperative complications following rectus fascia pubovaginal sling procedures.

In an effort to avoid the morbidity of rectus fascia slings, synthetic sling materials have been used. Serious complications of infection, erosion, and obstruction have occurred from the many different synthetic sling materials and designs that have been used. These include infections related to the implantation of a non-absorbable foreign body into the vagina as well as erosion of the synthetic sling into the urethra and vagina. The most notable of the synthetic sling material products was the Protegen® brand of synthetic sling that received wide media attention because of postoperative complications.

In an effort to avoid problems of infection with synthetic slings as well as morbidity with rectus fascia slings, cadaveric tissues were introduced as a sling material. Cadaveric fascia and cadaveric dermis have been used as an alternative to autologous rectus fascia. Most studies of cadaveric tissues show that these tissues do not have the long term durability of the rectus fascia tissue transplanted from the abdomen to the vagina of the same patient.

During recent years, a small filament polypropylene synthetic tape has become widely used in the contemporary art. The small filaments are associated with a low incidence of infection and erosion. The durability of the material appears to be good. The Tension-free Vaginal Tape (TVT)® utilizes a proline mesh tape that is woven with small proline filaments. The small diameter of the filaments appears to allow tissue ingrowth that prevents serious complications of synthetic non-absorbable sling materials that occurred in the past.

The TVT is surgically implanted in the patient using an instrument placed from the vagina and passed through the retropubic space to the suprapubic area. The difficulty in passing the instrument from the vagina to the suprapubic area has resulted in numerous serious complications from intra-operative injury to organs in the pelvis. Although the synthetic tape sling is tension free, many surgeons have difficulty achieving proper tension on the tape. For this reason, complications of recurrent urinary incontinence may occur in patients having too little sling tension and bladder outlet obstruction may occur in patients having too much sling tension on the tape.

The SPARC® modification of the TVT was developed to avoid the instrument complications that occur with TVT. The SPARC utilizes an instrument that is passed from the suprapubic area through the retropubic space into the vagina rather than from the vagina through the retropubic space to the suprapubic area as in the TVT. The SPARC instrument modification significantly reduces the potential for serious bowel and vascular injuries. Bladder perforation continues to be a problem for the SPARC modification, however cystoscopy is always done after the instrument is in position and the instrument is removed and repositioned if bladder perforation is identified. Both the TVT and SPARC are tension free tape pubovaginal sling procedures. The proline (polypropylene) mesh tape of the SPARC is almost identical to the proline mesh tape of the TVT. Surgeons continue to have difficulty intraoperatively with sling tension using these tape procedures. The SPARC was designed with a suture down the center of the sling that can be used to release excess sling tension intraoperatively. However, the suture modification for sling tension is rarely used by surgeons and intraoperative adjustment of sling tension continues to be a problem for both the TVT and the SPARC.

U.S. Pat. No. 6,406,423 (hereinafter "Scetbon") purports to disclose a modification to avoid the bladder perforation problem of both the TVT and the SPARC using the same type of synthetic suburethral tape used in the SPARC and TVT. The procedure uses a complex instrument system that is passed through the retropubic space under finger guidance, which is the same technique that has been used for rectus fascia slings procedures for many years. The morbidity of the transvaginal dissection of the retropubic space described in this procedure is identical to the rectus fascia sling procedures in the past. One of the objectives of current sling procedures is to avoid the paravaginal dissection required for the Scetbon technique. One of the reasons for the success of the TVT and the SPARC is that neither require paravaginal dissection described in the Scetbon modification. The mid-urethral positioning of the sling described in the TVT and SPARC is surgically difficult to accomplish from the approach described by Scetbon.

A biodegradable tape sling of the contemporary art has recently been introduced by Mentor, Inc. and is trademarked as SABRE®. The tape is a non-mesh synthetic biodegradable design consisting of a small patch attached to ends that have a saw-tooth pattern which hold the sling in position. The sling transfer instrument is larger in diameter than the SPARC instrument and has much less curvature. There is very little clinical experience at this time using this device. Historically, synthetic non-mesh slings have had a high incidence of erosion and infection. Although this product is biodegradable, it has the inherent short term risks of synthetic non-absorbable products since it represents a foreign body until it is absorbed.

Unlike the instant invention, all of the above pubovaginal sling designs involve using a narrow single layer tape sling. The TVT and SPARC sling are polypropylene mesh slings 1 cm wide that are placed in the mid-urethra of women who have urinary incontinence. The most common cause of stress urinary incontinence in women is altered anatomy of the urethra. A sling design is needed that can conform to the anatomical variations of the urethra of women who have urinary incontinence. Most women who have moderate to severe urinary incontinence have associated anatomical prolapse of the urethra and bladder. Some women have had multiple previous incontinence surgical procedures and have intense scar formation around the urethra. The intraoperative positioning of the narrow mesh tape in women who have anatomical distortion of the urethra from prolapse or previous surgery can be difficult. As evidenced in the above discussion of pubovaginal sling designs and sling transfer instruments, an improvement in sling design is essential for improvement in the success of incontinence surgery as well as for reduction of morbidity and complications. An improvement met and addressed via the teachings of the instant invention.

SUMMARY OF THE INVENTION

In the preferred embodiment of the present invention, a surgical instrument for treating female urinary stress incontinence comprising a) a tubular mesh sling for implanting into the lower abdomen of a female providing support to mid-urethral and bladder neck sphincteric continence sites, said sling defining in part plastic sheath portions fixedly attached to a tubular mesh section; and b) a tubular sling transfer instrument having a distal end and a proximal end, said instrument defining in part a progressively curved shaft portion positioned between distal and proximal ends with a handle located at its proximal end, a detachable tip positioned and angularly displaced from said curved shaft at its distal end, a means for attaching said detachable tip to said progressively curved shaft portion and a sling transfer collar which is removably attached to said detachable tip and said tubular mesh sling plastic sheath portions.

The tubular knit mesh pubovaginal sling of the instant invention is disclosed as a two layer single component configuration which allows the sling to conform to anatomical variations of the anterior vaginal wall and urethra that are commonly encountered during the surgical implantation of a pubovaginal sling in women who have prolapse of the bladder and urethra resulting in anatomical distortion of the urethra. During the surgical implantation of the tubular knit mesh pubovaginal sling, enhanced positioning beyond that afforded via the contemporary art and can be achieved by using forceps to "roll" the sling into the desired position along the urethra. This is especially important in women who have had previous vaginal surgery near the urethra that results irregular areas of scarring around the urethra and abnormal anatomical angulation of the urethra and the instant invention's unique construction design allows for the positioning accommodation of anatomical variance/distortion. In so doing, the tubular knit mesh pubovaginal sling further conforms to the anatomy of the urethra and anterior vaginal wall which is an important structural feature when the anatomy of the patient is distorted by urethral prolapse or previous vaginal surgery around the urethra.

Since normal women have a bladder neck sphincteric continence site and a mid-urethra sphincteric continence site, a wide tubular mesh sling design is disclosed that anatomically supports both sphincteric continence sites. The proximal part of the wide sling segment is positioned slightly above the bladder neck and the distal part of the wide sling segment is positioned slightly below the mid-urethra. The dual urethral continence site structure of the tubular knit mesh sling provides a significant continence advantage compared with other incontinence designs.

The instrument used for sling transfer has a reverse curve tip that is specifically designed to slide along the posterior surface of the pubic bone. It is designed to push the bladder away from the pubic bone and decrease the incidence of bladder perforation and pelvic organ injury resulting from sling transfer instrument placement.

The suprapubic sling transfer instrument is passed through the anterior abdominal wall to the anterior margin of the pubic bone. After passing through the anterior abdominal wall, the sling transfer instrument is passed directly over the upper edge of the pubic bone and the handle is rotated sharply upward to direct the reverse curve tip along the posterior surface of the pubic bone. As the tip is passed along the back of the pubic bone toward the lateral attachments of the vagina, any anatomical structures adhering to the pubic bone are pushed away by the reverse curve tip of the sling transfer instrument. This design modification is especially important in women who have had previous pelvic surgery and have anatomical structures adhering to the pubic bone because of scar tissue due to the previous surgery.

To position the sling, a 3.5 cm midline anterior vaginal incision is made that extends through the vaginal mucosa. The vaginal mucosa is separated away from the vaginal wall laterally to the pubic bone. The tip of the sling transfer instrument perforates the vaginal wall in the lateral part of the dissection. The sling transfer collar is placed on the sling transfer instrument. The sling transfer instrument is used to transfer the end of the sling to the suprapubic area on both the right and left sides. The center suture is used to position the sling in the center of the urethra and the suture is removed. The sling spacer is placed under the sling and the sling tension is adjusted. The tip of the sling is cut on each end and the plastic sheath is removed on each side. The sling spacer is removed and the excess sling is cut at the skin level in the suprapubic area. The vaginal mucosa is closed and a vaginal pack and Foley catheter are placed.

When transvaginal placement of the instrument is preferred, a transvaginal sling transfer instrument having the same design features as the suprapubic transfer instrument is used. The transvaginal sling transfer instrument is passed from the vagina along the posterior surface of the pubic bone to the suprapubic area. A semilunar transverse incision in the anterior vaginal wall is recommended for the transvaginal approach to allow the sling transfer instrument to be introduced from an anatomically lateral vaginal position. The sling transfer instrument needs to be introduced into the retropubic space from the lateral margin of the vagina. The transverse incision allows the tip of the sling transfer instrument to be placed against the posterior side of the pubic bone at the lateral margin of the vagina. From the lateral margin of the vagina, the sling transfer instrument can be passed in a straight line through the retropubic space against the posterior surface of the pubic bone to the suprapubic area. Once the sling transfer instrument on each side is passed through the retropubic space, the detachable tip of the sling transfer instrument is disconnected from the shaft of the sling transfer instrument and the sling transfer instrument is removed leaving the semi-rigid plastic sheath for transfer of the tubular mesh sling through the retropubic space to the suprapubic area.

In another readily envisioned embodiment, the tubular knit mesh sling is shaped to fit transvaginal placement using bone anchors, tissue anchors, and conventional sutures. The tubular mesh design can be fitted for cystocele repair, rectocele repair, and to anatomically support other tissues in the body. The disclosure of this structure applies to all tubular sling designs and includes but is not limited to all tubular knit or woven patterns. The material used in construction of the tubular sling includes all biocompatible synthetic polymers both biodegradeable and non-biodegradeable. The disclosure includes materials used in construction of a tubular sling composed of any organic or inorganic compound used singularly or in combination to produce an implantable tubular design used for anatomical support. The tubular sling design used for urethral and vaginal support is disclosed to contain tissue remodeling materials within the center segment when clinically indicated. Biodegradable tubular mesh sling may contain tissue remodeling materials including but not limited to homologous dermis, heterologous dermis, and porcine intestinal submucosa.

Given the deficiencies of the contemporary art and the enhancement teachings of the instant invention, it is an object of the instant invention to provide a tubular mesh sling for incontinence which eliminates urethral obstruction and wetting difficulties associated with slings and tapes of the contemporary art.

It is another object of the instant invention to provide an incontinence solution which avoids the morbidity associated with rectus fascia tissue transplanted from the abdomen to the vagina of a patient and the long term durability deficiencies of cadaveric tissue as used in the contemporary art.

It is a further object of the instant invention to provide an incontinence solution which avoids the numerous and serious complications from intra-operative injury to organs in the pelvis.

It is yet another object of the instant invention to avoid paravaginal dissection required of surgical instruments and methodologies associated with the contemporary art.

A further object of the instant invention is to provide an incontinence solution which is embodied as a sling design capable of conforming to the anatomical variations of the urethra of women who have urinary incontinence.

Yet another object of the instant invention is to disclose an incontinence solution by providing a tubular knit mesh pubovaginal sling and be rolled to the desired position along the urethra.

A yet further object of the instant invention is to provide a tubular knit mesh pubovaginal sling which conforms to the anatomy of the urethra and anterior vaginal wall when the anatomy of a patient is distorted by urethra prolapse or previous vaginal surgery.

Another object of the instant invention is to provide a two-layer tubular mesh sling in a single component structure that has an anterior surface which attaches to the vaginal wall adjacent to the urethra and a posterior surface which attaches to the vaginal mucosa.

An additional object of the instant invention is to provide an incontinence solution in a tubular mesh sling form which avoids buckling due to opposing forces of the vaginal wall and vaginal mucosa on the sling.

A further object of the instant invention is to provide a tubular mesh sling which has an anterior and posteriorial layer which provides greater tensile strength compared to tape mesh slings of the contemporary art.

Yet another object of the instant invention is to provide a tubular mesh sling design which demonstrates a significant degree of elasticity of the sling material.

A further object of the instant invention is to provide a tubular mesh sling which embodies a dual continence design and can be positioned to support both the mid-urethra and bladder neck sphincteric continence sites.

It is to be understood that both the foregoing general description and the following detailed description are exemplary and explanatory only, and are not restrictive of the invention as claimed. The accompanying drawings, which are incorporated herein by reference, and which constitute a part of this specification, illustrate certain embodiments of the invention and, together with the detailed description, serve to explain the principles of the present invention.

Further, the purpose of the foregoing abstract is to enable the U.S. Patent and Trademark Office and the public generally, and especially the design engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

In this respect, before explaining at least one embodiment of the invention in detail, it is to be understood that the invention is not limited in this application to the details of construction and to the arrangement so the components set forth in the following description or illustrated in the drawings. The invention is capable of other embodiments and of being practiced and carried out in various ways. Also, it is to be understood that the phraseology and terminology employed herein are for the purpose of description and should not be regarded as limiting. As such, those skilled in the art will appreciate that the conception, upon which this disclosure is based, may readily be utilized as a basis for the designing of other structures, methods and systems for carrying out the several purposes of the present invention. It is important, therefore that the claims be regarded as including such equivalent constructions insofar as they do not depart from the spirit and scope of the present invention.

DESCRIPTION OF THE DRAWINGS

FIG. 4B illustrates the tubular design of the mesh sling of the instant invention deployed as a vaginal wall support.

FIG. 5 illustrates the tubular sling transfer instrument for suprapubic sling placement of the instant invention.

FIGS. 11 through 11B illustrates in further detail the connection means for attaching the detachable tip of instruments illustrated in FIGS. 9 and 10.

FIG. 12 illustrates the tip attachment for attachable tip illustrated in association with FIGS. 9 and 10.

DESCRIPTION OF THE PREFERRED EMBODIMENT

While the making and using of various embodiments of the present invention are discussed in detail below, it should be appreciated that the present invention provides for inventive concepts capable of being embodied in a variety of specific contexts. The specific embodiments discussed herein are merely illustrative of specific manners in which to make and use the invention and are not to be interpreted as limiting the scope of the instant invention.

Figure 1:
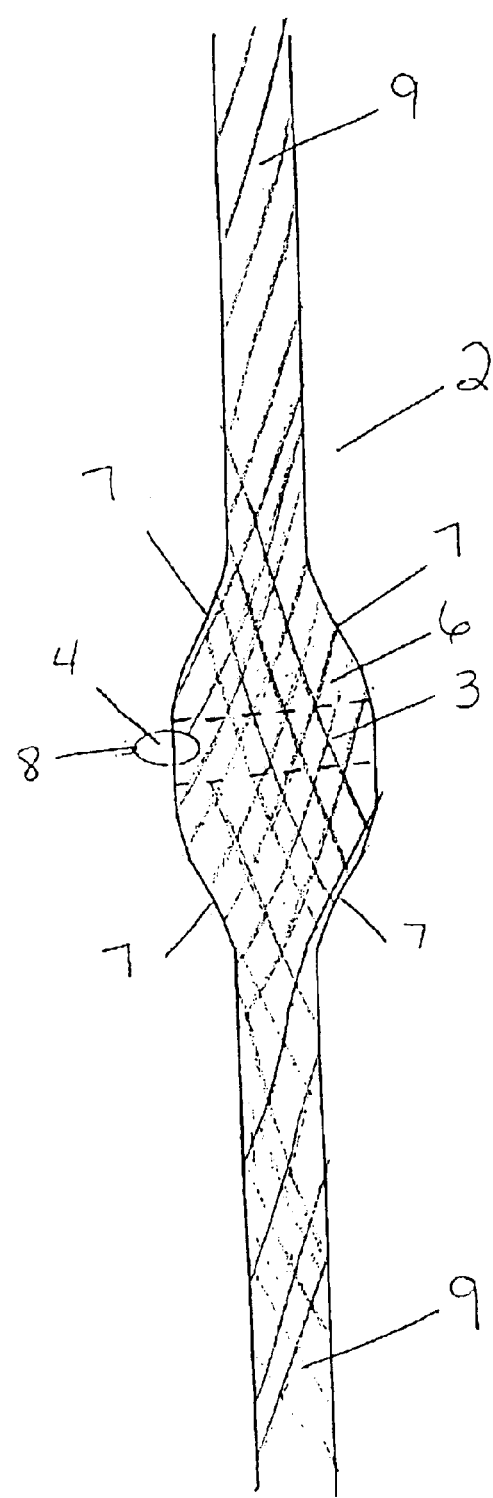
FIG. 1 illustrates the dual sphincteric continence design of the tubular mesh sling of the instant invention.

FIG. 1 illustrates the dual sphincteric continence design of the tubular mesh sling of the instant invention. Turning now to FIG. 1.

The mesh sling of the instant invention is generally referred to as element 2. As seen in FIG. 1, the mesh sling 2 of the instant invention is comprised generally of a central segment 6 and distal segments 9. The central segment 6 of the tubular mesh sling 2 is approximately 2.5 cm wide and 2.0 cm long with a rapid taper over approximately 1.5 cm down to a size of 1.0 cm in width at its distal ends 9. A suture 8 is placed in the center of the sling 2 to indicate the area to be located over the center of the urethra. Each distal section 9 of the sling 2 is covered with a circular plastic sheath which extends and overlaps 3 in the central segment 6 approximately at the position of the suture 8. The plastic sheath 3 as well as the center suture 8 are removed at the end of the implementation procedure. Though variable and appropriate dimensions may be had with respect to the sling of the instant invention, deployment is most effective when practiced at an approximate length of 60 cm and 2.5 cm in width to position and support the bladder neck sphincteric and mid-urethral sphincteric continence sites.

Figure 1A:
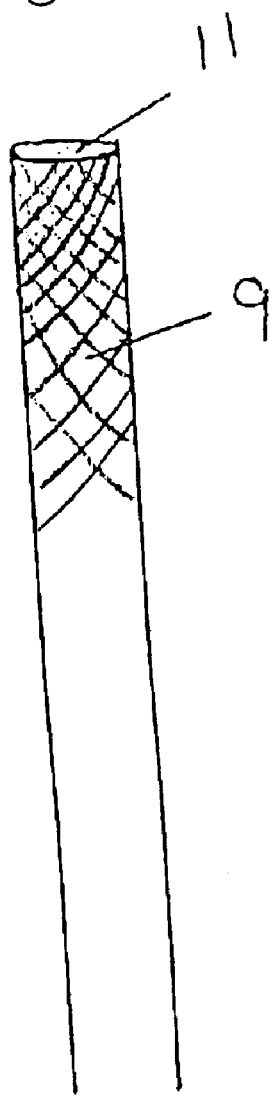
FIG. 1A illustrates further detail with respect to the distal segment and tubular configuration of the pubovaginal sling of the instant invention.
Figure 1B:
FIG. 1B illustrates an end portion of each distal section of the sling in FIGS. 1 and 1A.

FIG. 1A illustrates further detail with respect to the distal segment and tubular configuration of the pubovaginal sling of the instant invention. FIG. 1B illustrates an end portion of the distal segments. Turning now to FIGS. 1A and 1B. As shown in FIG. 1A a distal end 9 of the tubular mesh sling of the instant invention wherein the tubular shape 11 of the sling may be observed. Said tubular shape 11 allowing the sling to conform to anatomical variations of the urethra are encountered during surgical procedures of urinary incontinence. Though appropriate and variable dimensioning may be readily envisioned and accommodated as required, the diameter of the ends of the tubular shape 11 is approximately 1.0 cm. The sling construction is of a knit mesh which will be discussed further in association with FIG. 2.

Figure 1C:
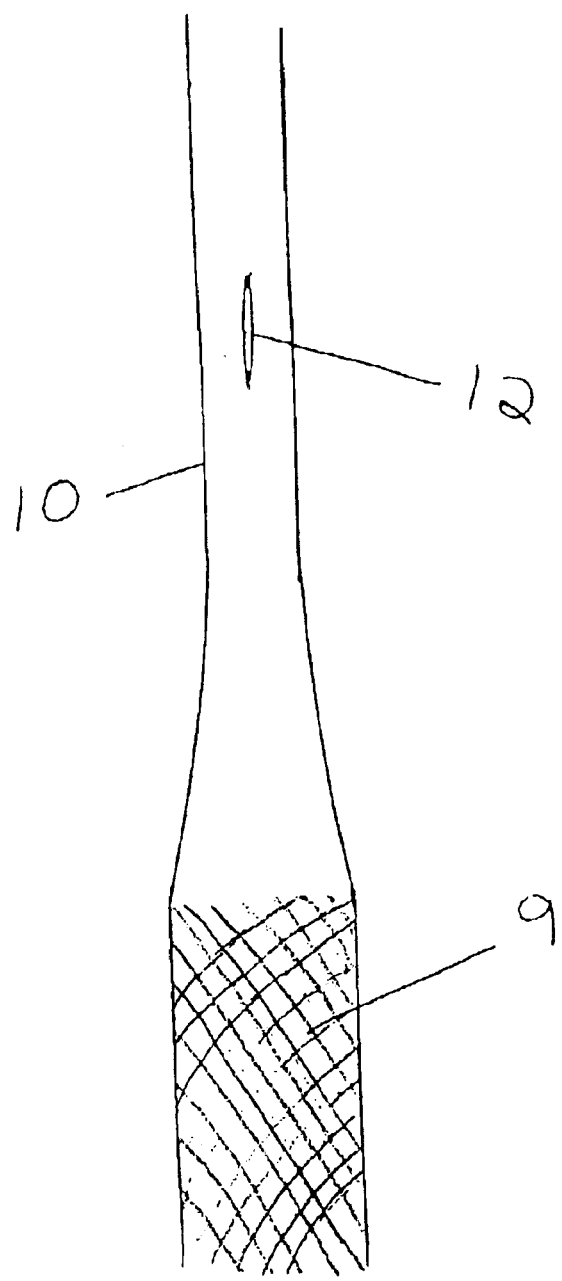
FIG. 1C illustrates in further detail the semi-rigid plastic transfer sheath which is bonded to the tubular mesh sling of the instant invention.
Figure 2:
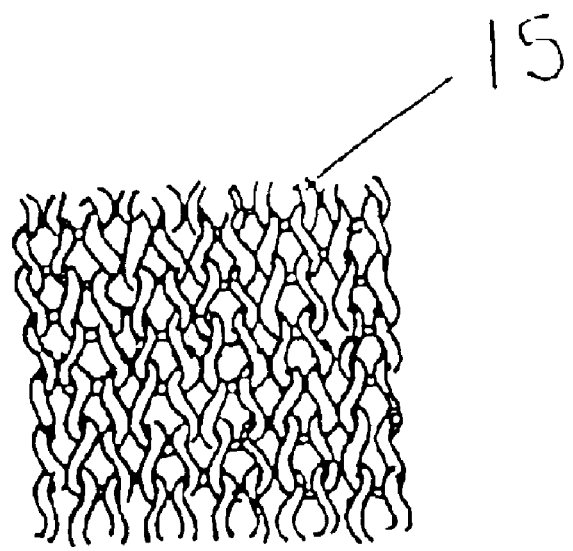
FIG. 2 illustrates a simple knit pattern of the tubular knit mesh sling of the instant invention.

FIG. 1C illustrates in further detail the semi-rigid plastic transfer sheath which is bonded to the tubular mesh sling of the instant invention. Turning now to FIG. 1C. As can be observed in FIG. 1C, the tubular mesh sling used in association with transvaginal sling placement further consists of a plastic sling transfer sheath 10 which is bonded to the tubular mesh sling 9 with said plastic sling transfer sheath 10 further embodying a slit 12 approximately 1.0 cm in length for insertion therein of a sling transfer instrument used in association with transvaginal sling placement. Said tubular sling transfer instrument for suprapubic sling placement discussed and disclosed in further detail in association with FIG. 5. Further observation with respect to the knit mesh patterns associated with mesh sling embodiment are discussed in association with FIG. 2. Turning now to FIG. 2.

FIG. 2 illustrates a simple knit pattern of the tubular knit mesh sling of the instant invention. In FIG. 2 a single knit mesh pattern 15 is illustrated for purposes of full and enabling disclosure. Such knit patterning provides the sling with stretch properties that allow the tubular shape of the sling to conform to the urethra and to prevent the sling from being positioned with excessive tension. The elastic properties of the sling allow the patient to void following surgery without complications of long term urinary retention. As disclosed in association with FIG. 2 only one illustrative embodiment of mesh patterning is provided. However, no such limitation is intended in form. Patterns of filaments of knit pattern can be a simple knit, complex knit or woven pattern. Such knit pattern may have seams or may be seamless with the size of the filaments dependent on the clinical application and chemical composition of the knit. For non-absorbable polymers, such as polypropylene, a filament size of approximately 0.006 inch is suggested. For slow degradation absorbable polymers, such as polylactate, the filament size of approximately 0.015 inch is suggested. To those skilled in the art, it will become readily apparent that for rapidly absorbable biopolymers, a larger filament size can and should be practiced.

Figure 3:
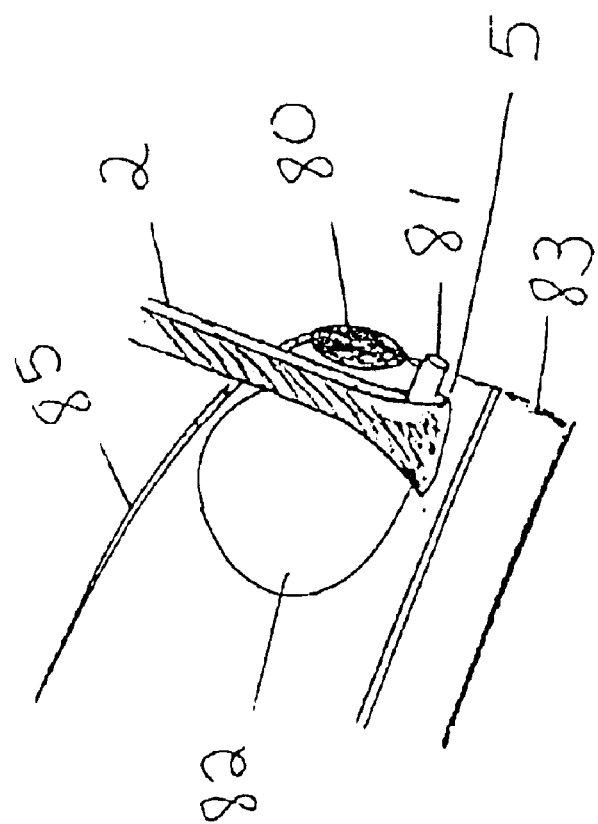
FIG. 3 illustrates an anatomical sagittal section illustrating employment of the tubular mesh sling of the instant invention.

FIG. 3 illustrates an anatomical sagittal section illustrating employment of the tubular mesh sling of the instant invention. As can be seen in FIG. 3, the tubular mesh sling of the instant invention 2 is shown positioned with its center section 5 positioned to support dual sphincteric incontinence site. For purposes of full and enabling disclosure, the tubular mesh sling 2 of the instant invention is shown in positional association with the vagina 83, urethra 81, bladder 82, abdominal wall 85 and pubic bone 80.

Figure 4:
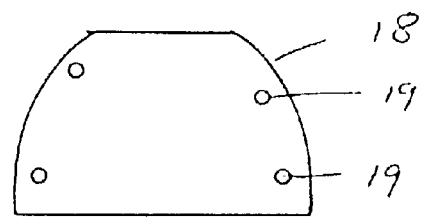
FIGS. 4 and 4A illustrate alternative embodiments for the tubular mesh sling of the instant invention for vaginal wall support and transvaginal placement.
Figure 4A:
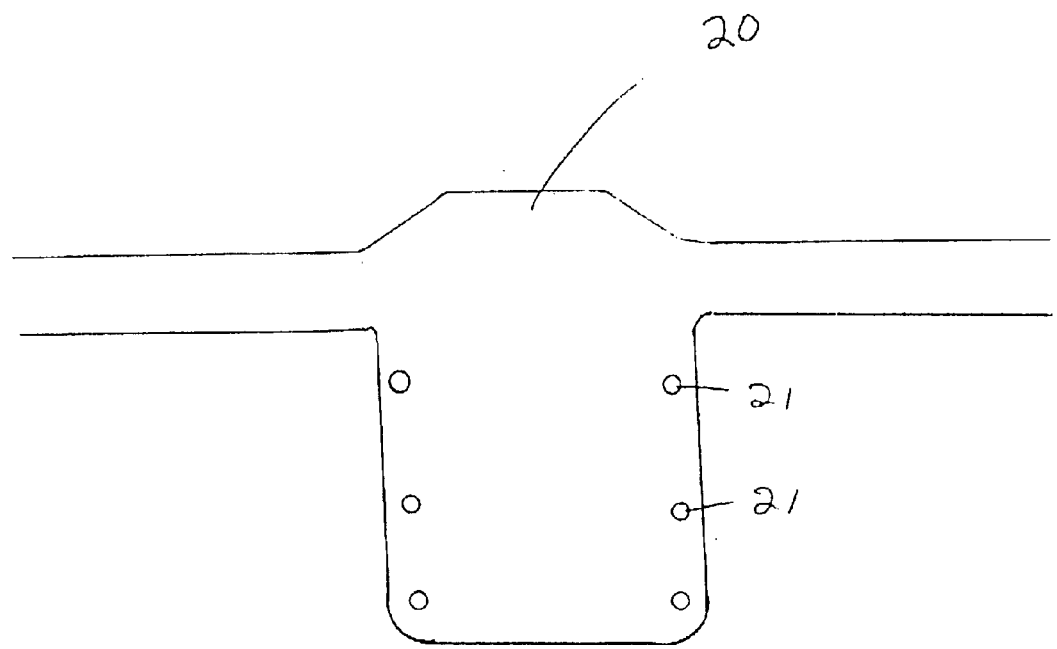

FIGS. 4 and 4A illustrate alternative embodiments for the tubular mesh sling of the instant invention for vaginal wall support and transvaginal placement. Turning now to FIGS. 4 and 4A. In FIG. 4 a tubular mesh sling for vaginal wall support 18 is disclosed. Said embodiment further illustrated with eyelet for sutures and tissue anchors 19. In FIG. 4A, a tubular mesh sling for transvaginal placement 20 is disclosed for vaginal wall and urethral support with sutures and tissue anchors 21.

FIG. 4B illustrates the tubular design of the mesh sling of the instant invention deployed as a vaginal wall support. Turning now to FIG. 4B. FIG. 4B illustrates the positioning for tubular design for vaginal wall support wherein the tubular mesh sling for anterior vaginal wall support 18 is shown in positional relationship to the urethra 81 and pubic bone 80.

Figure 6:
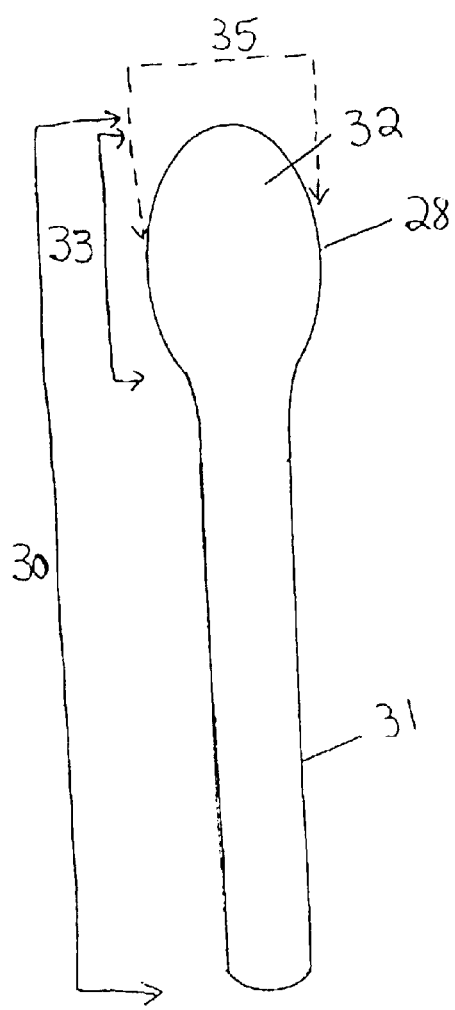
FIG. 6 illustrates in further detail the sling transfer instrument handle.

FIG. 5 illustrates the tubular sling transfer instrument for suprapubic sling placement of the instant invention. Turning now to FIG. 5. In FIG. 5 tubular sling transfer instrument for suprapubic sling placement is generally indicated as 20, with the shaft portion of the sling transfer instrument is approximately 3.5 mm in diameter. The tubular sling transfer instrument 20 for supra pubic sling placement has a progressive curvature of its shaft 26 with the diameter of the curvature of the sling transfer instrument 20 being approximately 20 cm. As practiced, the maximum radius of the progressively curved shaft 26 is 5.1 cm with said curvature being progressive from a handle portion 28 to a tip portion 29. A reverse curve 27 is placed on the instrument's tip 29. The length of said reverse curve 27 is approximately 1.0 cm in length. The tip 29 of the sling transfer instrument is approximately 0.5 cm in width. Reverse angle tip 29 is designed to slide along the posterior surface of the pubic bone as it is passed through the prevesical space. The width of the tip is approximately 5 mm which creates a channel for the sling. The progressive curvature of the shaft of the instrument 26 from the handle to the tip a sharper angle of curvature toward the tip 29 and a straighter angle of curvature toward the handle 28. The shaft's curvature 26 is designed to maintain the reverse curve on the tip against the posterior surface of the pubic bone as the instrument is being passed through the retropubic space during the operation. The surface of the shaft may be smooth metal or it may have an illuminous surface. A thumb control of the handle 28 (not illustrated in FIG. 5) allows the surgeon to accurately guide the tip of the instrument 29 through the pelvis without having to observe the tip of the instrument. Said thumb control and additional handle features illustrated in association with FIG. 6. Turning now to FIG. 6.

Figure 6A:
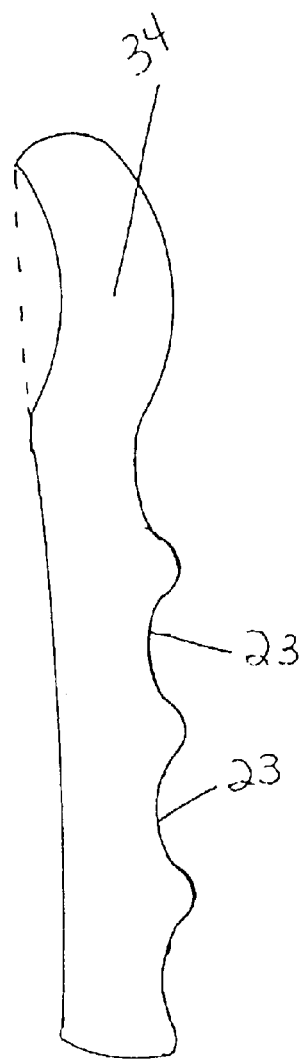
FIG. 6A illustrates another view providing additional detail of the handle of FIG. 6.

FIG. 6 illustrates in further detail the sling transfer instrument handle. In FIG. 6, the handle 28 allows the surgeon to control the tip of the sling transfer instrument as it is being passed through the pelvis of the patient. The handle 28 is approximately 12 cm in length 30 and 1.2 cm in width 31. Thumb control tip 32 is approximately 3.5 cm in length 33, 1.5 cm in depth 34 and 2.4 cm in width 35. One or more groove-like accommodations 23 (FIG. 6A) provide at least one accommodation 23 to allow the positioning therein of a finger to further guide the sling transfer instrument handle during operational deployment.

Figure 7:
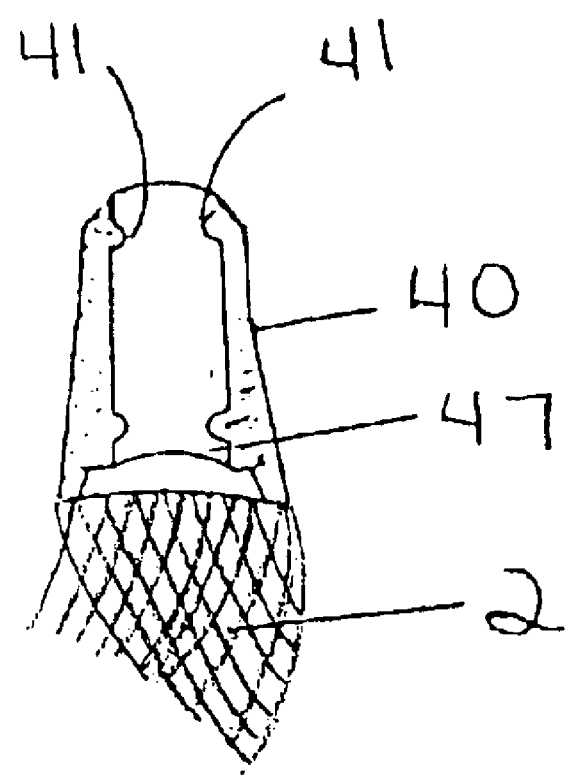
FIG. 7 illustrates the tubular sling transfer collar.
Figure 7A:
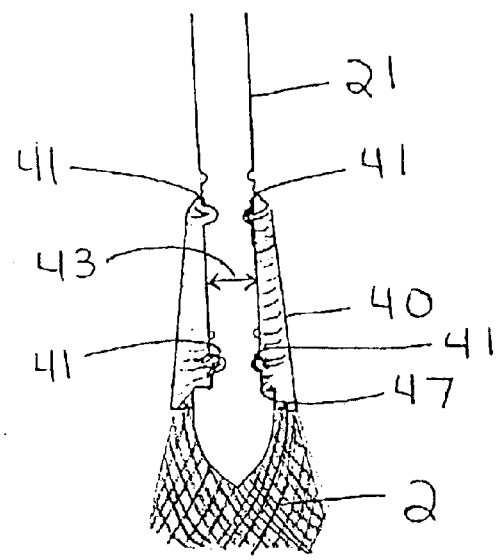
FIG. 7A illustrates a tubular sling transfer collar engaged with sling transfer instrument.

FIG. 7 illustrates the tubular sling transfer collar used in association with suprapubic sling placement. Turning now to FIG. 7. In FIG. 7 the sling transfer collar 40 is disclosed illustrating its transfer collar stabilizing tab 41 and positional connection thereto of the tubular mesh sling of the instant invention 2. Stabilizing tabs 41 allows the collar 40 to fit directly over the shaft of the sling transfer instrument (discussed and disclosed further in association with FIG. 8). The stabilizers 41 typically are arranged in opposition on each side of a collar edge 47 that fits over the sling transfer instrument with such tabs 41 snapping into corresponding grooves on the shaft of the sling instrument as shown in association with FIG. 8. After the collar 40 has snapped to the grooves in the shaft on the sling instrument, the collar slides down the shaft and the bottom of the collar rests upon tip of the transfer instrument. Turning now to FIG. 7A wherein the tubular sling transfer collar is illustrated and engaged with the sling transfer instrument.

FIG. 7A illustrates a tubular sling transfer collar engaged with sling transfer instrument. In FIG. 7A the sling transfer collar 40 is shown attached to the sling transfer instrument shaft 21. As discussed earlier in association with FIG. 5, the shaft of the sling transfer instrument is approximately 3.5 mm in diameter and the transverse diameter of the tip is approximately 5 mm. The tubular sling transfer collar is shown engaged with the sling transfer instrument with an opening 43 in the collar of approximately 3.5 mm in width which corresponds to the diameter of the shaft of the sling transfer instrument. Also shown in FIG. 7A, collar stabilizing tabs 41 that fit around the shaft 21 of the transfer instrument and made to fit in the groove in the tip of the sling transfer instrument 47 where it is engaged for sling transfer. The collar 40 is attached to the sling 2 at its one end and is transferred from the vagina to the suprapubic area after it is engaged with the sling transfer instrument.

Figure 8:
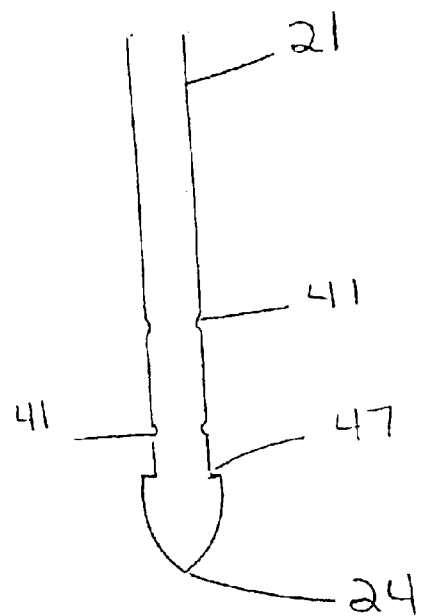
FIG. 8 illustrates for purposes of further detail the tip of the sling transfer instrument for suprapubic placement.

FIG. 8 illustrates for purposes of further detail the tip of the sling transfer instrument for suprapubic placement. Turning now to FIG. 8. As illustrated in FIG. 8, the shaft 21 of the sling transfer instrument is disclosed as are grooves 41 in the lateral sides of the shaft 21 of the sling transfer instrument. Further illustrated is the groove for sling transfer collar seating 47 and the tip of the sling transfer instrument 24.

Figure 9:
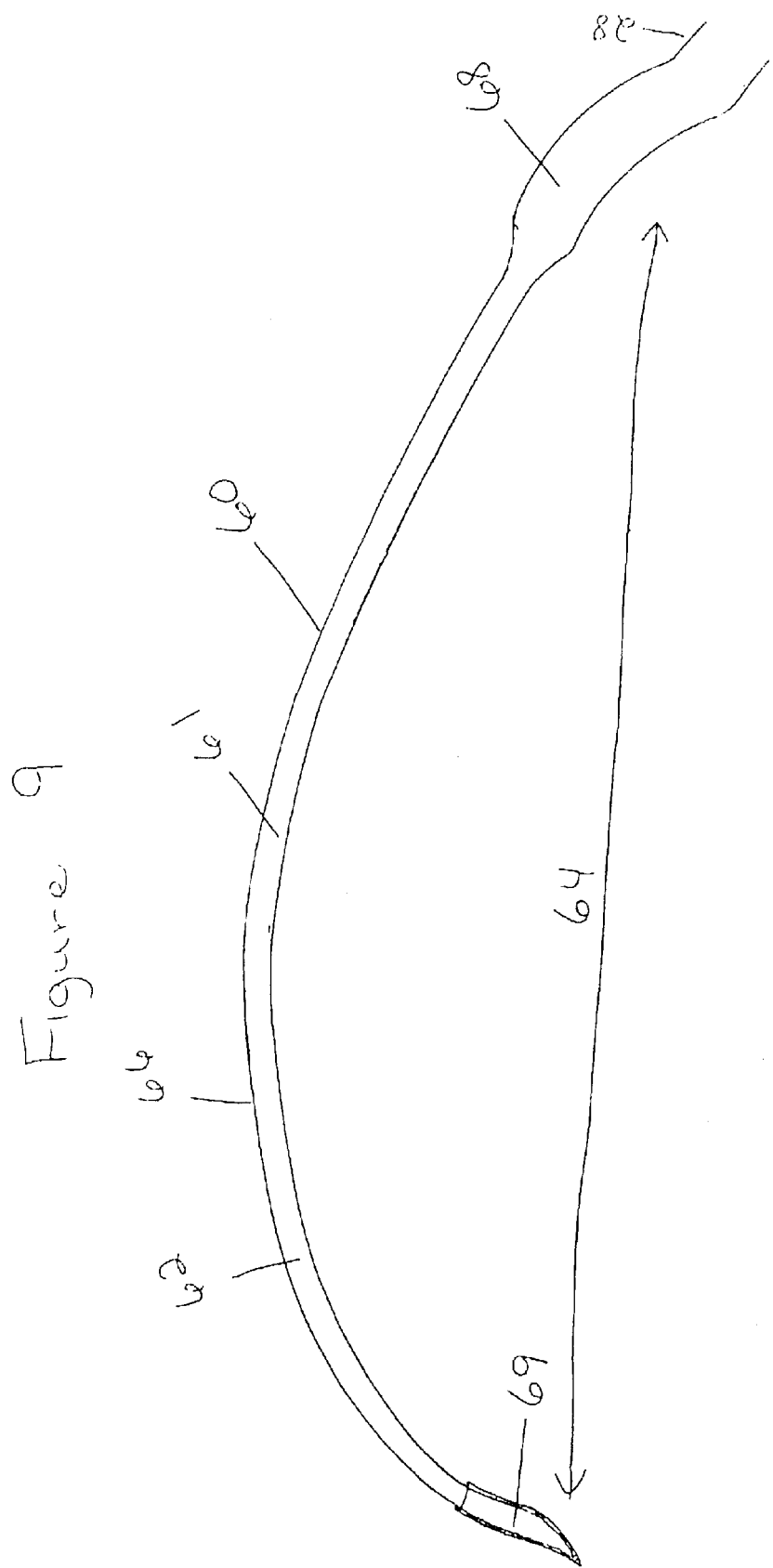
FIG. 9 illustrates for purposes of full and enabling disclosure, the transvaginal tubular sling transfer instrument.

FIG. 9 illustrates for purposes of full and enabling disclosure, the transvaginal tubular sling transfer instrument is used in association with transvaginal deployment of the mesh sling of the instant invention. Turning now to FIG. 9. The transvaginal sling transfer instrument 60 has the same curvature and tip configuration as the suprapubic sling transfer instrument disclosed in association with FIG. 5. With respect to the transvaginal sling transfer instrument, however, the tip 69 can be detached from the shaft 61 via circular rotation. Also shown in association with FIG. 9 is the handle 68 and progressive curvature 66 of the instrument. The diameter of the progressive curvature is approximately 20.0 cm. The thumb segment 68 of the handle 28 is attached to the proximal end of the shaft 61 with the tip 69 of the sling instrument being detachable. The body of the tip is approximately 1.0 cm in length and the reverse curve segment of the tip is approximately 1.0 cm in length for a total length of 2.0 cm for the detachable tip of the sling transfer instrument 60. The diameter of the shaft of the sling transfer instrument closest to the tip is approximately 3.5 mm. At 2.0 cm proximal to the detachable tip the diameter of the sling transfer instrument is approximately 3.6 mm. The dimensioning of the transvaginal sling transfer instrument provides rigidity of the instrument to allow perforation of the anterior rectus fascia that occurs near the end of the retropubic pass of the sling transfer instrument. The progressive curvature design 66, the reverse curve of the tip 69 and the handle 68 are the same for both the transvaginal sling transfer instrument and the suprapubic sling transfer instrument, recognizing suprapubic sling transfer instruments tip is not detachable in construction.

Figure 10:
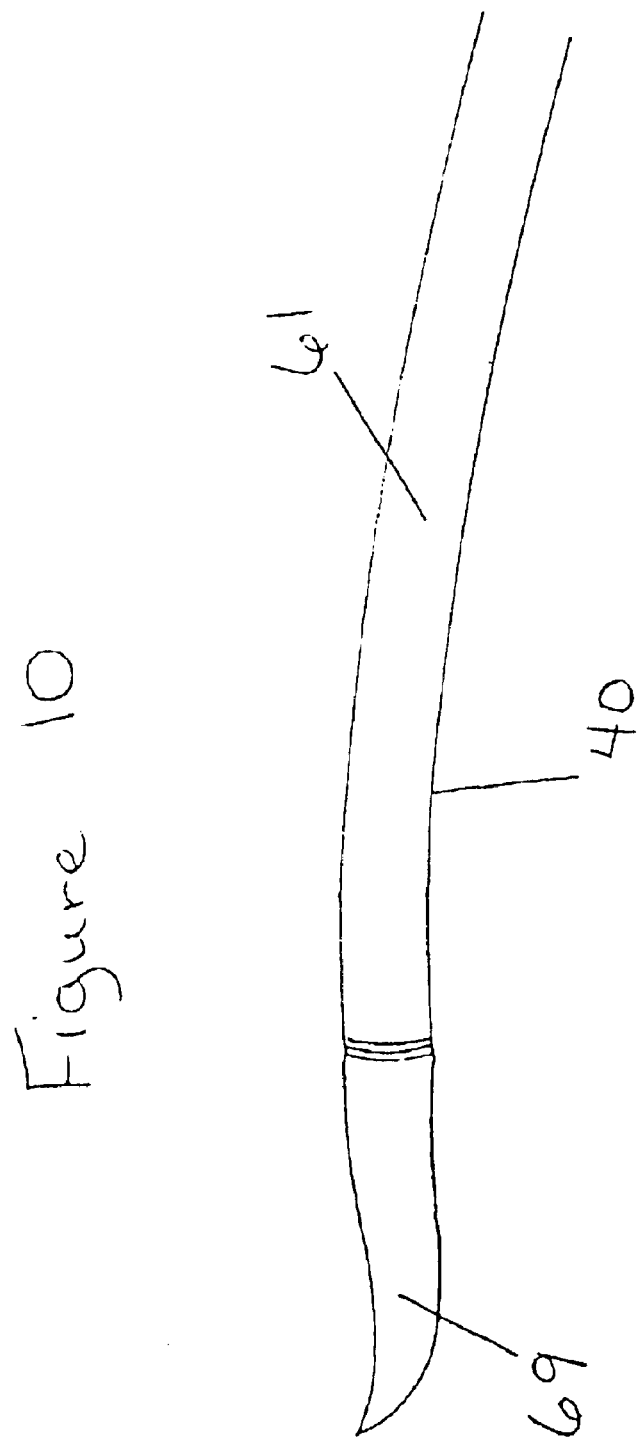
FIG. 10 illustrates in further detail the detachable tip of the sling transfer instrument of FIG. 9.

FIG. 10 illustrates in further detail the detachable tip of the sling transfer instrument of FIG. 9. A tubular semi-rigid plastic sheath 40 is attached to the detachable tip 69 of the sling transfer instrument. The plastic used in association with the semi-rigid plastic sheath is approximately 0.2 mm in thickness and is attached circumferentially to the tip 69. The outside diameter of the tip at the level of attachment of the tubular plastic sheath 40 is approximately 3.9 mm with the outside diameter of the plastic sheath proximal to the detachable tip being 4.0 mm.

FIG. 11 illustrates in further detail the connection means for attaching the detachable tip of instruments illustrated in FIGS. 9 and 10. Turning now to FIG. 11. In FIG. 11 it is observed where the detachable tip 69 is approximately 3.9 mm in diameter at its proximal end 71. The reverse curve segment 72 is approximately 1.0 cm in length and the body 73 of the detachable tip is 1.0 cm in length with a total length of the detachable tip 69 being approximately 2.0 cm. The detachable tip 69 is connected to the tip of the shaft 61 of the sling transfer instrument 60. As can be readily observed in association with FIGS. 11A and 11B, connectors 75 on the tip of the sling transfer instrument are received into a connection means 76 located on the internal portion of open ended portion of tip 69. Said connection allowing the selected disengagement of the tip from the shaft of the sling transfer instrument. The diameter of the shaft of the sling transfer instrument is approximately 3.5 mm near tip of the shaft 61 and the diameter of the detachable tip is approximately 3.9 mm. The thickness of the semi-rigid plastic sheath is 0.2 mm with a diameter of the opening in the center approximately 3.5 mm. The shaft of the sling transfer instrument 61 increases in size through the distal 2.0 cm to a diameter of 3.6 mm. The semi-rigid plastic sheath increases in diameter through that same length to approximately 4.0 mm. The semi-rigid plastic sheath may be clear or it may contain illuminous material within the wall of the sheath. A tip attachment used in association with the detachable tip of the sling transfer instrument discussed in association with FIGS. 9, 10, 11A and 11B is illustrated in FIG. 12. Turning now to FIG. 12.

FIG. 12 illustrates the plastic tip attachment 90 which is used in association with the detachable tip after it has perforated the skin in the suprapubic area. The tip attachments 90 is shaped to snap on to the detachable end of the sling transfer instrument with said attachment being approximately 1.9 cm in diameter and 4.0 cm in length. A small circumferential groove 96 is placed on the bottom of the tip attachment 90 to fit snugly around the semi-rigid tubular plastic segment near the proximal end of the detachable tip for transfer of the sling. After the tip attachment is snapped into place via connection snapping means 92, 94 and hinge means 95, a partial rotation of the tip counterclockwise will detach the detachable tip from the sling transfer instrument.

Figure 13:
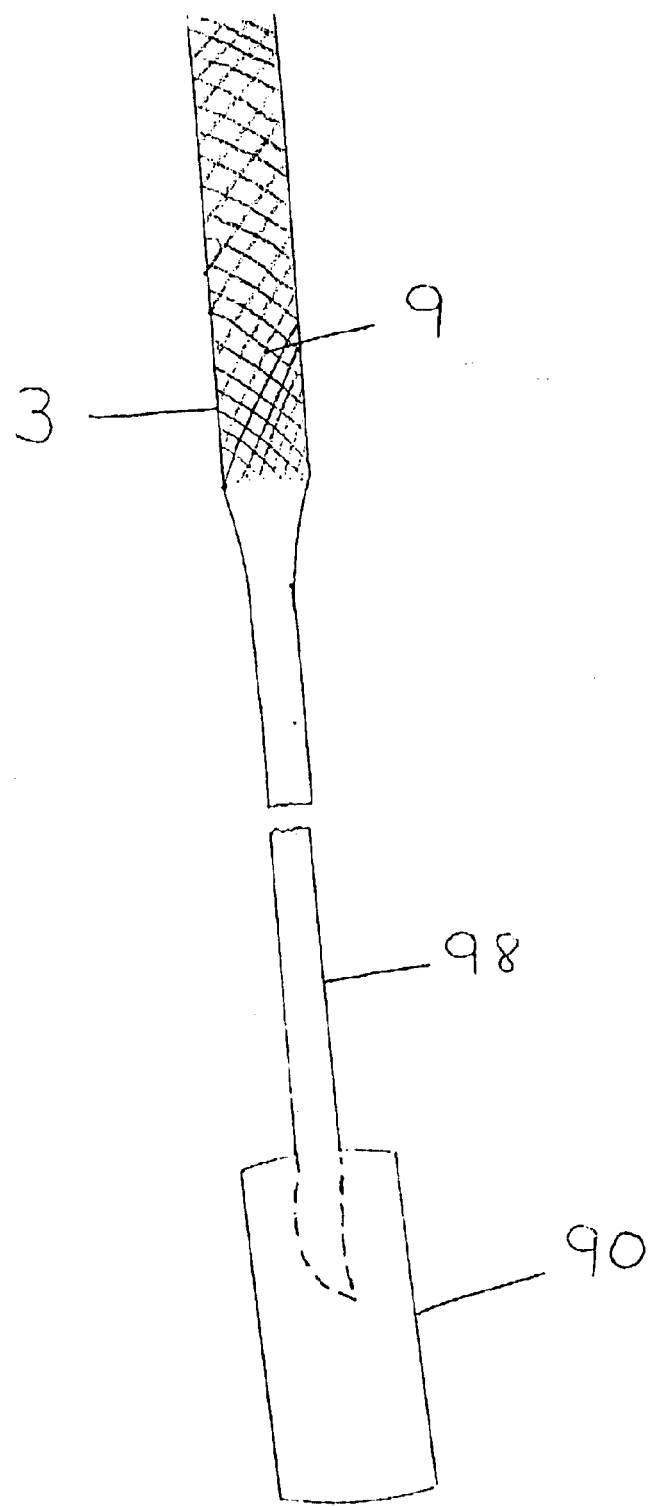
FIG. 13 illustrates the transvaginal tubular sling transfer design in further detail.

FIG. 13 illustrates in further detail the transvaginal tubular sling transfer design used in association with the transvaginal transfer instrument discussed and disclosed in association with FIGS. 9 through 12. Turning now to FIG. 13. In FIG. 13 it is disclosed where plastic tip attachment 90 can be used to pull a tubular semi-rigid plastic transfer sheath 98 through the retropubic space. The tubular plastic sheath 98 is directly connected to the tubular mesh sling 9. Said plastic attachment 90 used to position the tubular mesh sling 9 into the place. In FIG. 13, a plastic tip attachment 90 completely encases a detachable tip of the sling transfer instrument (shown in phantom). The tubular mesh sling 9 is connected to the tubular plastic sheath 98 which gradually widens from approximately 4.0 mm to 10.0 mm before the tubular mesh sling is connected to the tubular plastic sheath 98.

Figure 14:
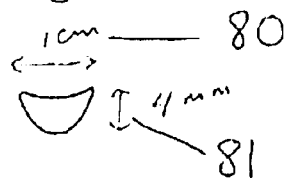
FIGS. 14, 14A and 14B illustrates the tubular sling spacer of the instant invention.
Figure 14A:
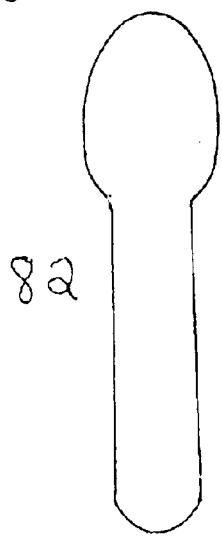
Figure 14B:
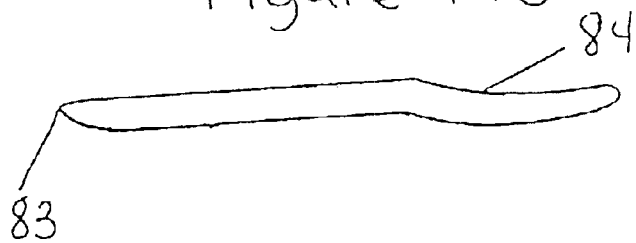

FIGS. 14, 14A and 14B illustrates the tubular sling spacer of the instant invention. The spacing device of the instant invention is designed to maintain a tension-free sling during placement which avoids excessive tension and the complications of long-term urinary retention. As can be easily envisioned by those skilled in the art, the sling spacer dimensions can vary according to different applications. As seen in FIGS. 14, 14A and 14B, the sling spacer body 82 is approximately 4.0 cm in length with an 0.5 cm tip 83. The handle 84 of the device is approximately 2.5 cm in length. The width of the device 80 is approximately 1.0 cm and it is approximately 4.0 mm in thickness 81.

Method of Suprapubic Approach to Sling Placement

Step 1

The initial step in placement of the tubular mesh sling is preparation of the vagina for correct positioning of the sling around the urethral. The patient is prepped an draped for the surgical procedure. A weighted vaginal speculum is placed to visualize the anterior vaginal wall for the initial incision. A Foley catheter is placed into the bladder through the urethra. The balloon on the Foley catheter is inflated with 5 cc of water. Mild traction is placed on the Foley catheter and the balloon is palpated through the anterior vagina. The distal part of the Foley balloon represents the location of the bladder neck. This specific location is marked on the anterior vagina using a marking pen. Saline containing antibiotic is injected just beneath the vaginal mucosa to elevate the mucosa from the underlying vaginal wall. This is done to facilitate dissection of the vaginal mucosa off the vaginal wall. A 3.5 cm vertical incision is made in the anterior vagina extending through the vaginal mucosa. Of the 3.5 cm anterior vaginal incision, 1 cm is above the transverse line made with the marking pen that identifies the bladder neck and 2.5 cm is below the transverse line. The incision will expose the anatomical location of the bladder neck sphincteric continence site and the mid-urethral continence site.

Both a cutting and spreading technique is done using dissecting scissors to separate the vaginal mucosa from the underlying vaginal wall. The vaginal mucosa is separated from the vaginal wall laterally to the margin of the pubic bone on both the right and left side.

Step 2

The suprapubic area is palpated to locate the anterior margin of the pubic bone. The midline of the body at the level of the pubic bone is marked with the marking pen. Three cm lateral to the midline overlying the pubic bone, a 4 mm transverse incision is made in the skin on both sides. The sling transfer instrument is passed through the skin incision and passed through the subcutaneous tissues down to the pubic bone. The tip of the sling transfer instrument is directed to the upper edge of the pubic bone. The tip is manipulated to slide over the upper edge of the pubic bone through the attachment of the rectus fascia. As the sling transfer instrument perforates the anterior rectus fascia, the handle of the sling transfer instrument is rotated upward toward the head of the patient. This maneuver positions the tip of the sling transfer instrument against the posterior surface of the pubic bone. The reverse curve tip of the sling transfer instrument is held firmly against the posterior surface of the pubic bone. The sling transfer instrument is advanced through the retropubic space toward the vaginal incision below. As long as the tip of the sling transfer instrument is held firmly against the posterior pubic bone as it is advanced, it is almost impossible to perforate the bladder or other pelvic organs. Since the surgeon cannot see the anatomic course of the tip of the sling transfer instrument, it is the tactile sensations of the handle that guide the surgeon to advance the tip in the direction of the vaginal incision. If the surgeon is right handed, the right hand is on the handle of the sling transfer instrument and the left index finger is in the vaginal incision. The left index finger can palpate the tip of the sling transfer instrument well before it perforates the urethropelvic ligament and anterior vaginal wall. Once the tip of the sling transfer instrument can be palpated through the vaginal incision, the surgeon can use the handle to guide the tip into the lateral part of the vaginal incision which will insure that the sling transfer instrument tip will exit in the exact desired location relative to the urethra and bladder.

Step 3

Both the right and left sling transfer instrument are passed from the suprapubic position into the vagina. When both the right and left sling transfer instrument has been passed into the vagina, cystoscopy is performed to confirm that no injury has occurred to the bladder. The tubular sling transfer collar is placed on the sling transfer instrument on both the right and left side. The sling transfer instrument on each side is pulled back through the retropubic space transferring the end of the tubular sling to the suprapubic location.

Step 4

The sling spacer is placed through the vaginal incision and positioned along the anterior vaginal wall. The ends of the sling in the suprapubic area are pulled to position the sling in the anterior vaginal wall. The central suture in the sling is used to center the sling on the urethra. The plastic sheath around the ends of the sling are removed. The sling spacer is removed. The location of the sling is checked. Tissue forceps are used to roll the tubular sling if position adjustment is needed. The final location of the sling is 0.5 cm proximal to the original bladder neck line made with the marker at the beginning of the operative procedure. The tubular sling extends distally 2.0 cm from the bladder neck to support the mid-urethra.

Step 5

When the anatomical position of the tubular mesh sling has been confirmed, the excess sling in the suprapubic area is cut at the skin level and a dressing is placed over the two small incisions. The vaginal mucosa is closed with interrupted sutures and a vaginal pack is placed. The Foley catheter and vaginal pack are left in place for 6 hours and both are removed.

Step 6

The patient is discharged when satisfactory voiding occurs.

Method of Transvaginal Approach to Sling Placement

Step 1

A transverse semilunar incision is made in the anterior vaginal wall at the mid-urethral level. The vaginal mucosa is dissected from the underlying vaginal wall proximally above the bladder neck.

Step 2

The sling transfer instrument is introduced in the lateral margin of the incision and placed below the pubic bone. The sling transfer instrument is passed in a straight line toward the suprapubic location. The reverse curve tip of the sling transfer instrument is held tightly against the posterior pubic bone during the pass of the tip from the vagina to the suprapubic area. When the anterior rectus fascia is reached with the tip of the sling transfer instrument, careful firm pressure is placed on the handle to perforate the anterior rectus fascia. This is the most resistance encountered during the passing of the sling transfer instrument. The sling transfer instrument is passed to the skin and a knife is used to make a small incision in the skin at the location of the tip of the sling transfer instrument to allow the sling transfer instrument to pass through the skin to the outside. The sling transfer instrument passing is done the same way on both the right and left sides.

Step 3

Cystoscopy is done to verify that no injury has occurred to the bladder.

Step 4

After cystoscopy is performed, the plastic sling transfer instrument tip attachment is snapped around the sling transfer instrument tip. A counterclockwise turn is done on the tip to disengage the tip from the shaft of the sling transfer instrument.

Step 5

The shaft of the sling transfer instrument on both sides is removed from the semi-rigid tubular plastic sheath.

Step 6

The plastic tip attachment is used to pull the sling into position on both sides.

Step 7

The sling spacer is placed between the anterior vaginal wall and the sling. When the sling tension has been adjusted using the sling spacer, the sling and the tubular plastic sheath is cut 4 cm above the skin in the suprapubic area. The plastic sheath on both sides is removed by grasping them with a hemostat and gently removing each. The tubular plastic sheath on each side is not connected at the level of the central suture and each side is easily removed. The sling spacer is removed. The central suture is cut and removed.

Step 8

The tubular mesh sling is cut at the skin level in the suprapubic area. The transverse vaginal incision is closed. A vaginal pack is placed and a Foley catheter is placed.

Step 9

Both the Foley catheter and the vaginal pack are removed 6 hours postoperatively and the patient is discharged after successful voiding.

The claims and specifications describe the invention presented and the terms that are employed in the claims draw their meaning from the use of such terms in the specification. The same terms employed in the prior art may be broader in meaning than specifically employed herein. Whenever there is a question between the broader definition of such terms used in the prior art and the more specific use of the terms herein, the more specific meaning is meant.

While this invention has been described to illustrative embodiments, this description is not to be construed in a limiting sense. Various modifications and combinations of the illustrative embodiments as well as other embodiments will be apparent to those skilled in the art upon referencing this disclosure. It is therefore intended that this disclosure encompass any such modifications or embodiments.

It will of course be understood that various changes may be made in form, details, arrangement and proportions of the apparatus without departing from the scope of the invention, which generally stated consists of an apparatus capable of carrying out the objects above set forth, in the parts and combination of parts as disclosed and defined in the appended claims.

We claim:

1. A surgical instrument for treating female urinary stress incontinence comprising:

a. a tubular mesh sling for implanting into the lower abdomen of a female providing support to mid-urethral and bladder neck sphincteric continence sites, said sling defining in part plastic sheath portions fixedly attached to a tubular mesh section; and b. a tubular sling transfer instrument having a distal end and a proximal end, said instrument defining in part a progressively curved shaft portion positioned between distal and proximal ends with a handle located at said proximal end, a detachable tip positioned and angularly displaced from said curved shaft at its distal end, a means for attaching said detachable tip to said progressively curved shaft portion and a sling transfer sheath which is attached to said detachable tip and said tubular mesh sling.

2. The tubular sling transfer instrument of claim 1 wherein said progressively curved shaft portion further comprises at least one seating channel for attaching a sling transfer collar.

3. The tubular sling transfer instrument of claim 1 wherein said handle further comprises a thumb control accommodation, said accommodation dimensioned approximately 2.5 and 4.5 cm in length and 1.0 and 1.5 cm in width.

4. The tubular sling transfer instrument of claim 1 wherein said handle further comprises at least one groove-like accommodation to allow the positioning therein of a finger.

5. The tubular mesh sling of claim 1 further comprising a spacing device used to position said sling to support mid-urethral and bladder neck sphincteric continence sites.

6. The tubular mesh sling of claim 1 wherein said mesh portion is comprised of non-absorbable polymers and filaments of said mesh have a diameter from about 0.002 inch to about 0.008 inch.

7. The tubular mesh sling of claim 1 wherein said mesh portion is comprised of absorbable polymers and filaments of said mesh have a diameter from about 0.012 inch to about 0.017 inch.

8. The tubular mesh sling of claim 1 wherein said mesh portion is approximately 2.5 cm in length, approximately 1.5 cm to 3.0 cm at its widest and generally center most position and approximately 1.0 cm wide at each of its opposite ends.

9. The tubular mesh sling of claim 1 wherein said plastic sheath portions further comprise an approximate 1.0 cm slit to receivably accommodate said sling transfer instrument.

10. The tubular transfer instrument of claim 1 wherein said progressively curved shaft portion has a diameter from about 3.5 mm to about 4.0 mm and a progressive curve with a maximum radius of approximately 5.1 cm.

11. The tubular transfer instrument of claim 1 wherein said detachable tip portion is curved and attached to said shaft portion in a direction opposite that of said shaft's curved portion, said detachable tip portion being approximately 1.0 cm in length and approximately 4.0 mm in width at an end opposite that end attached to said shaft portion.

12. The tubular transfer instrument of claim 1 wherein said handle is approximately 12 cm in length and 1.2 cm in width and further comprises within said length and length dimensions a contoured thumb control section approximately 3.5 cm in length, approximately 1.5 cm in depth and 2.4 cm in width.

13. The surgical instrument of claim 1 further comprising a tubular sling spacer which allows maintaining tension free deployment of said tubular mesh sling.

14. A surgical instrument for treating female urinary stress incontinence comprising:
   a) a tubular mesh sling for implanting into the lower abdomen of a female providing support to mid-urethral and bladder neck sphincteric continence sites, said sling defining in part plastic sheath portions fixedly attached to opposite ends of a tubular mesh section; and
   b) a tubular sling transfer instrument having a distal end and a proximal end, said instrument defining in part a progressively curved shaft portion positioned between distal and proximal ends with a handle located at said proximal end, a tip positioned angularly displaced from said curved shaft at its distal end, a means for attaching said angularly displaced tip to said tubular mesh sling plastic sheath portions.

15. The tubular sling transfer instrument of claim 14 wherein said progressively curved shaft portion further comprises at least one seating channel for attaching a sling transfer collar.

16. The tubular sling transfer instrument of claim 14 wherein said handle further comprises a thumb control accommodation.

17. The tubular sling transfer instrument of claim 14 wherein said handle further comprises at least one groove-like accommodation to allow the positioning therein of a finger.

18. The tubular mesh sling of claim 14 wherein said mesh portion is comprised of non-absorbable polymers and filaments of said mesh have a diameter from about 0.002 inch to about 0.008 inch.

19. The tubular mesh sling of claim 14 wherein said mesh portion is comprised of absorbable polymers and filaments of said mesh have a diameter from about 0.012 inch to about 0.017 inch.

20. The tubular mesh sling of claim 14 wherein said mesh portion is approximately 2.5 cm in length, approximately 2.5 cm at its widest and generally center most position and approximately 1.0 cm wide at each of its opposite ends.

21. The tubular mesh sling of claim 14 wherein said plastic sheath portions further comprises an approximate 1.0 cm slit to receivably accommodate said sling transfer instrument.

22. The tubular transfer instrument of claim 14 wherein said progressively curved shaft portion has a diameter from about 3.5 mm to about 4.0 mm and a progressive curve with a maximum radius of approximately 5.1 cm.

23. The tubular transfer instrument of claim 14 wherein said tip portion is curved and attached to said shaft portion in a direction opposite that of said shaft's curved portion, said tip portion being approximately 2.0 cm in length and approximately 4.0 mm in width at an end opposite that end attached to said shaft portion.

24. The tubular transfer instrument of claim 14 wherein said handle is approximately 12 cm in length and 1.2 cm in width and further comprises within said length and length dimensions a contoured thumb control section approximately 3.5 in length, approximately 1.5 cm in depth and 2.4 cm in width.

25. A method for treating female urinary incontinence comprising the steps of:
   a) providing a tubular sling transfer instrument having a distal end and a proximal end, defining in part a progressively curved metallic shaft portion positioned between distal and proximal ends and a tubular mesh sling attached thereto;
   b) passing the tubular sling transfer instrument and tubular mesh sling having dimensionally distinguishable mid-urethral and bladder neck sphincteric continence support sections into the body via the vagina to form a sling around mid-urethral and bladder neck sphincteric continence sites; and
   c) leaving the tubular mesh sling implanted in the body.

26. The method of claim 25 wherein said provided tubular sling transfer instrument is defined in part by a progressively curved shaft comprised of a bio-compatible polymer positioned between distal and proximal ends of said sling transfer instrument.

27. A method for treating female urinary incontinence comprising the steps of:
   a) providing a tubular sling transfer instrument having a distal end and a proximal end, defining in part a progressively curved metallic shaft portion positioned between distal and proximal ends; and
   b) passing the tubular sling transfer instrument into the body via a suprapubic approach into the vagina;
   c) positioning a tubular sling transfer collar attached to a tubular mesh sling having dimensionally distinguishable mid-urethral and bladder neck sphincteric continence support sections onto the tubular sling transfer instrument;
   d) partially withdrawing the sling transfer instrument to position each end of the tubular sling to a suprapubic position;
   e) positioning the sling in the anterior vaginal wall;
   f) removing a plastic sheath from each end of the tubular sling; and
   g) leaving the tubular sling implanted in the body.

28. The method of claim 27 further comprising the steps of:
   a) inserting through a vaginal incision a sling spacer and positioning said spacer along the anterior vaginal wall;
   b) rolling or otherwise motivating the tubular string for positioning adjustment;
   c) removing the sling spacer; and
   d) trimming excess tubular sling material.

29. The method of claim 27 wherein said provided tubular sling transfer instrument is defined in part by a progressively curved shaft comprised of a bio-compatible polymer positioned between distal and proximal ends of said sling transfer instrument.

* * * * *